United States Patent [19]

Marty

[11] Patent Number: 4,699,778

[45] Date of Patent: Oct. 13, 1987

[54] COSMETIC COMPOSITIONS

[75] Inventor: Jean-Pierre Marty, Montesson, France

[73] Assignee: Roussel Uclaf, Paris, France

[21] Appl. No.: 726,028

[22] Filed: Apr. 23, 1985

[30] Foreign Application Priority Data

Apr. 26, 1984 [FR] France ............................. 84 06559

[51] Int. Cl.$^4$ ........................... A61K 7/42; A61K 9/08
[52] U.S. Cl. ..................................... 424/59; 514/844; 514/859; 514/861; 514/885; 514/886; 514/887
[58] Field of Search ................. 435/68, 638; 514/886, 514/848; 424/59

[56] References Cited

U.S. PATENT DOCUMENTS 4,154,821  5/1979  Drouet et al. .......................... 514/8
4,346,109  8/1982  Yamatsu et al. ..................... 514/886

Primary Examiner—Dale R. Ore
Attorney, Agent, or Firm—Bierman and Muserlian

[57] ABSTRACT

Improved cosmetic compositions for skin care containing an amount sufficient for skin care of glycoprotein extracts of lysed microbial bodies of Hafnia species or strains prepared by (a) cultivating a microbial Hafnia strain until complete development of microbial bodies, (b) subjecting the microbial bodies to lysis, (c) treating the lysate with at least one solvent for delipidation and depigmentation of the lysate, (d) dissolving the resulting product, (e) subjecting the solution to centrifugation and (f) optionally subjecting the resulting product to ultrafiltration and a method of improving a person's skin.

10 Claims, 1 Drawing Figure

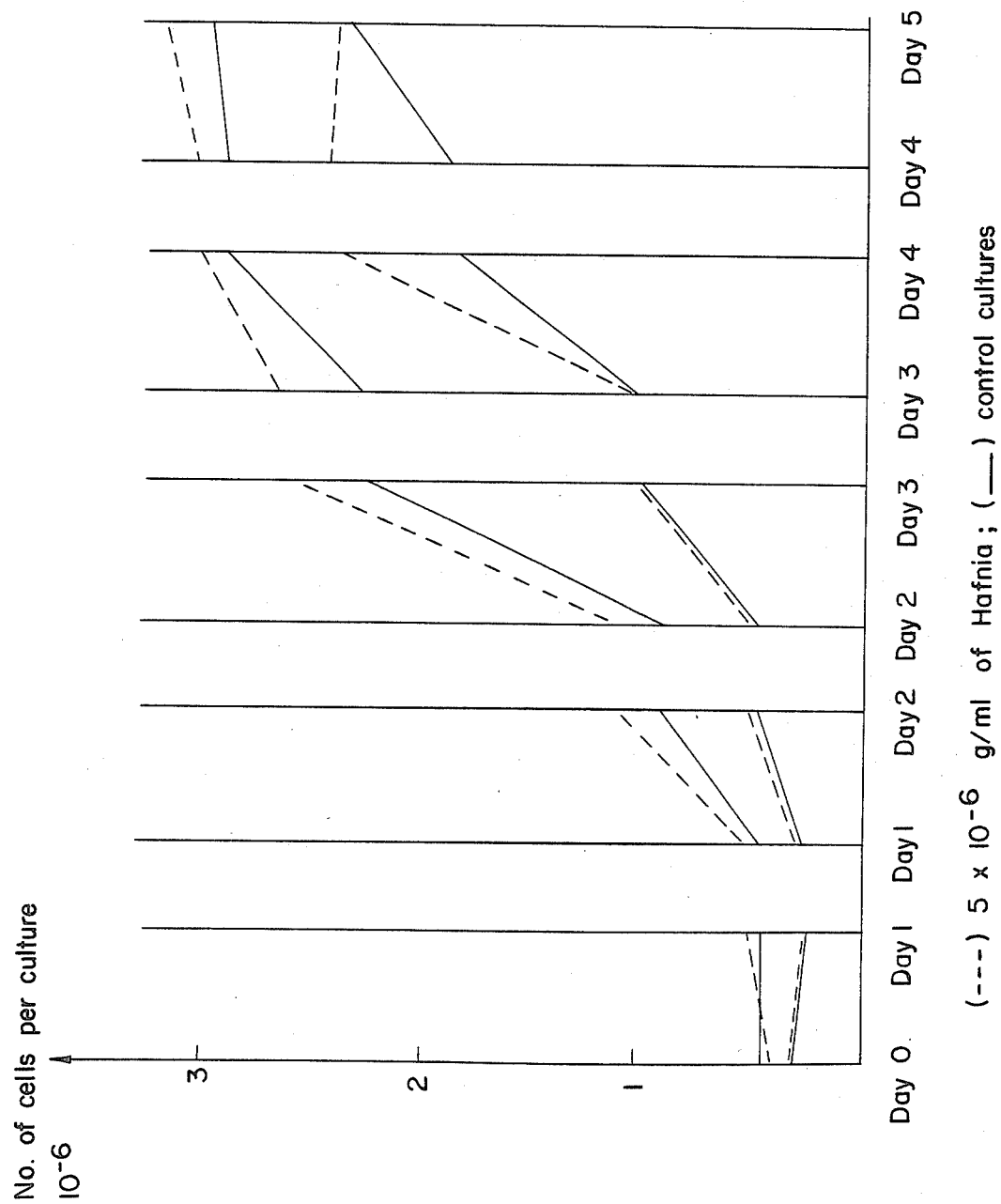
Diagram of cumulative results on the effect of lysed Hafnia extracts on the cellular growth of fibroblasts in culture

COSMETIC COMPOSITIONS

STATE OF THE ART

Commonly assigned U.S. Pat. No. 4,154,821 describes the glycoproteins used in the cosmetic compositions of the invention in which the glycoproteins obtained after lysis of the Hafnia bodies are subjected to ultrafiltration with a membrane to obtain glycoproteins with a molecular weight of at least 300,000. The patent describes the said glycoproteins as having anti-inflammatory and immunostimulating activity.

OBJECT OF THE INVENTION

It is an object of the invention to provide novel cosmetic compositions for skin care.

It is another object of the invention to provide a novel method of caring for skin.

These and other objects and advantages of the invention will become obvious from the following detailed description.

THE INVENTION

The novel cosmetic compositions of the invention for skin care contain an amount sufficient for skin care of glycoprotein extracts of lysed microbial bodies of Hafnia species or strains prepared by (a) cultivating a microbial Hafnia strain until complete development of microbial bodies, (b) subjecting the microbial bodies to lysis, (c) treating the lysate with at least one solvent for delipidation and depigmentation of the lysate, (d) dissolving the resulting product, (e) subjecting the solution to centrifugation and (f) optionally subjecting the resulting product to ultrafiltration. Preferably the compositions of the invention contain glycoproteins extracts obtained as above but not having been subjected to ultrafiltration.

For the first time, the invention shows that the said bacterial extracts possess a remarkable cutaneous anti-irritant activity and are endowed with a stimulating activity on cellular growth. Moreover, the glycoprotein extracts of lysed Hafnia microbial bodies protect the skin against exterior effects such as sunlight, heat, cold, detergents and pollution.

The compositions of the invention can be used to soothe irritated skin whatever the cause. For example, the compositions of the invention can be applied to soothe skin which has a tendency to acne. In particular, when applied in the morning, they calm the sensations of stinging and burning caused by local medical treatments for acne applied in the evening which are often very irritating. They can also be used to calm the redness of sunburn and also to protect the skin effectively from exterior attacks and therefore are advantageously used to protect skin made sensitive by disorders such as blotchiness or rosacea. Moreover, the cutaneous regenerative properties of the compositions, by stimulating the cellular growth, makes them effective in combatting ageing of the skin.

The compositions of the invention contain glycoproteins obtained by lysis of the Hafnia bodies whether or not subjected to a final ultrafiltration. The final ultrafiltration described in U.S. Pat. No. 4,154,821 is a dialfiltration using a porous membrane presenting a threshold of retention of substances having a molecular weight equal to or greater than 300,000. In fact, the membrane used can present a different threshold of retention with the choice of the latter depending on the substances to separate.

The preferred cosmetic compositions of the invention are those that contain glycoprotein extracts of lysed Hafnia microbial bodies not having been subjected to final ultlrafiltration. These glycoproteins correspond to the intermediate products obtained by Step C of Examples 1 and 2 of U.S. Pat. No. 4,154,821. The physiochemical characteristics of these glycoproteins are given in Example 1 of the experimental part.

In the compositions of the invention, the Hafnia extract can be used in powder form or in the form of an aqueous solution and preferably the cosmetic compositions contain $5 \times 10^{-5}\%$ to 1% by weight of glycoprotein extracts of the lysed Hafnia microbial bodies.

In addition to the lysed Hafnia extracts, the compositions of the invention can also contain other active compounds having particular cutaneous properties. Thus, the compositions of the invention can also contain oleyl acetate which has anti-lipase properties and directly prevents the formation of comedos and blackheads. The said compositions contain two constituents which by their combined action constitute a product well adapted to skins with a tendency to acne.

The compositions of the invention can also contain a compound favoring cicatrisation of acne lesions such as for example, extracts of Centella Asiatica and more particularly a glycol extract of Centella Asiatica. Other substances such as oenothera oil and amino acids can also be incorporated into the compositions.

The cosmetic compositions of the invention can be in any of the forms used in cosmetic science such as cream or gel in pots or tubes, milk, oil, or lotion in glass or plastic bottles and possibly in measuring bottles, phials or aerosols. For each form, the appropriate excipients are used which must have all the usually required qualities. They must be endowed with a great affinity for the skin, be well tolerated, stable, present an adequate consistency enabling easy and pleasant ultilisation.

Examples of suitable excipients are derivatives of palmitates and stearates, triglycerides of fatty acids, lanolin, glycerin, propylene glycol (cream), ethyl alcohol (lotion), vegetable, animal or mineral oils, waxes, moisturizers, thickeners, stabilizers, and emulsifiers currently in use.

If desired, the compositions of the invention can also contain filters, screens against solar radiation, blockers of free radicals and singlet oxygen, vitamin extracts, perfumes, preservatives, anti-oxidants, colorings.

The novel method of the invention for caring for a person's skin comprises applying to a person's skin a comestic composition containing an amount sufficient for skin care of glycoprotein extracts of lysed microbial bodies of Hafnia species or strains prepared by (a) cultivating a microbial Hafnia strain until complete development of microbial bodies, (b) subjecting the microbial bodies to lysis, (c) treating the lysate with at least one solvent for delipidation and depigmentation of the lysate, (d) dissolving the resulting product, (e) subjecting the solution to centrifugation and (f) optionally subjecting the resulting product to ultrafiltration.

In the following examples there are described several preferred embodiments to illustrate the invention. However, it should be understood that the invention is not intended to be limited to the specific embodiments.

EXAMPLE 1

The bacterial extract of Hafnia strain No. 5731 of the Pasteur Institute of Paris France obtained by Step C of Examples 1 and 2 of U.S. Pat. No. 4,154,821 had the following characteristics:
(a) Appearance: light beige water soluble powder
(b) Elementary analysis:
  Carbon 31.6% ±3
  hydrogen 4.9% ±0.6
  nitrogen 6.6% ±0.4
(c) Nature and proportion of various constituents expressed as a mean ±typical deviation (*):
  proteins: 26.4% (±5.2*)
  glucides: neutral hexoses 18.3% (±3.7*); uronic acids 0.6% (±0.9*); osamines 8.7% (±2.4*)
  ribonucleic acids 17.4% (±2.35*)
  desoxyribonucleic acids 5.4% (±2.1*)
  humidity 8%
(d) Ultra-violet spectrum The ultra-violet spectrum traced between 190 nm and 350 nm at 125 mcg/ml was standard for a product containing proteins (Do 0.73 +0.2) and nucleic acids (1.4±0.4).

(e) Chromatography of gel filtration

Chromatography of gel filtration on Sephacryl S 300 in an 0.1 M ammonium carbonate buffer revealed the presence of 3 molecular families:
  1 family of high molecular weight ≧300,000 of glycoproteic nature.
  2 families of molecular weight close to 12,000 of nucleic acid nature.

EXAMPLE 2

A face cream was prepared containing the following ingredients:
  "Hafnia" extract 0.5 g
  oleyl acetate 2.0 g
  diethanolamine alkyl phosphate 2.0 g
  ethyl hexyl palmitate 8.0 g
  hydrogenated lanolin 5.0 g
  triglycerides of fatty acids 4.0 g
  sorbitan stearate 1.0 g
  carboxyvinyl polymer 0.4 g
  preservatives 0.4 g
  aromatic composition 0.4 g
  purified water q.s. for 100 g

EXAMPLE 3

A face gel was prepared containing the following ingredients:
  "Hafnia" extract 0.5 g
  glycol extract of Centella Asiatica 5.0 g
  propylene glycol 5.0 g
  carboxyvinyl polymer 0.8 g
  preservatives 0.35 g
  aromatic composition 0.1 g
  purified water q.s. for 100 g

EXAMPLE 4

A body cream was prepared containing the following ingredients:
  "Hafnia" extract 0.2 g
  glycerol stearate 4.0 g
  sorbitan palmitate 6.0 g
  perhydrosqualene 5.0 g
  isopropyl palmitate 7.0 g
  triglycerides of fatty acids 9.0 g
  glycerine 5.0 g
  preservatives 0.35 g
  aromatic composition 1.0 g
  purified water q.s. for 100 g

EXAMPLE 5

A tonic face lotion was prepared containing the following ingredients:
  "Hafnia" extract 0.05 g
  propylene glycol 5.0 g
  preservatives 0.3 g
  aromatic composition 0.1 g
  ethyl alcohol 10.0 g
  purified water q.s. for 100 ml

EXAMPLE 6

A sun-tan milk was prepared containing the following ingredients:
  "Hafnia" extract 0.1 g
  solar filters 5.0 g
  vaseline oil 10.0 g
  isopropyl palmitate 9.0 g
  silicon oil 2.5 g
  cetyl ether P.O.E. 2.0 g
  sorbitan stearate 1.0 g
  preservatives 0.35 g
  aromatic composition 0.5 g
  purified water q.s. for 100 ml

PHARMACOLOGICAL DATA (A) Cutaneous tolerance

The backs of six albino rabbits of RIVER strain were shaved over an area of about 14×14 cm and on each side of the vertebral axis, three parallel incisions were made by scarifying. 0.5 ml of a cream containing 0.05% of lysed Hafnia extract described in Example 1 was then applied to the skin (scarified and non-scarified area) on the right hand side with the left hand side acting as control. The cutaneous irritation was assessed 24 to 72 hours respectively after application of the product. The observations were made on the two scarified and non-scarified zones according to the numbered scale indicated in the Official Journal of Feb. 21, 1982.

Erythema and formation of scabs:
  no erythma 0
  slight erythema, hardly visible 1
  erythema quite visible 2
  moderate to severe erythema 3
  severe erythema (crimson red) with the formation of light scabs, deep lesions 4
Formation of edema:
  no edema 0
  very slight edema, hardly visible 1
  slight edema, (contours well defined, visible swelling) 2
  medium edema (thickness about 1 mm) 3
  severe edema (more than 1 mm thick and extending beyond the shaved area) 4

The primary irritation index assessment was determined by adding up the figures obtained for erythema and edema, after 24 hours and 72 hours, on the one hand in the six non-scarified zones and on the other hand in the six scarified zones. Then, the average was calculated by dividing the total by 24 and this average represented the cutaneous primary irritation index (PI):
  non-irritant PI≦0.5
  slightly irritant 0.5<PI≦2
  moderate irritant 2<PI≦5 very irritant $5 < PI \leq 8$

The total of these results shows that by using the official scale the cream containig 0.05% of lysed Hafnia extract had a cutaneous irritation index $PI < 0.5$, that is it was a non irritant.

(B) Action on the cellular growth of fibroblasts in culture

A solution of containing Hafnia glycoproteins of Example 1 containing $5 \times 10^{-6}$ g/ml was tested on a culture of fibroblasts of human embryo prepuce. The culture medium used was a medium containing various amino-acids, vitamins, inorganic salts, glucose, serum from veal foetus and antibiotics (Penicillin, Streptomycin, Fungizone, Kanamycin, biotin) and the medium was buffered with sodium bicarbonate and the pH was adjusted to 7.2. The cultures were inoculated to a concentration of $40 \times 10^3$ cells per ml in culture flasks for tissue of different surfaces and the cultures were placed in an incubator thermostatically controlled at 37° C. in which the atmosphere was regulated in $CO_2$ (5%).

To carry out a numeration and evaluation of the cellular growth, the fibroblasts had to be detached from the culture support by the action of a trypsin solution. The numeration was carried out with a phase-contrast microscope and the living cells appear refracting.

FIG. 1 shows the total of the experiments carried out at a dose of $5 \times 10^{-6}$ g/ml compared with the control cultures. In all the experiments, the addition of the solution based on lysed Hafnia extracts stimulated the cellular growth.

(C) Effect on cutaneous erythema in guinea pigs exposed to ultraviolet radiation 20 male guinea pigs of HARTLEY strain weighing between 350 and 400 grams had their costal region shaved and the hair was removed over an area of 6 cm $\times$ 3 cm. Solar erythema was effected with UV irradiation by a quartz tube lamp for therapeutic use. To avoid UV irradiation of all the animal, the latter was placed in a corset of thick material containing 4 circular perforations of 8 mm. diameter each (=irradiation spots). In two of these spots (the other two serving as controls), 0.25 ml of a cream containing lysed Hafnia extract of Example 1 was applied immediately after the exposure at concentrations of 0.01% and 0.05% by weight.

Two hours after the irradition, the intensity of the erythema obtained in the spots was noted on a scale of 0 to 3.

Evaluation
0 No erythema
1 spot just visible
2 erythema more noticeable
3 erythema very visible The average degree of erythema for each group was established and the percentage of protection in relation to the control spots was expressed thus.

$$\frac{\text{Average of the valuation of the controls} - \text{Average of the valuation of those treated}}{\text{Average of the control valuation}} \times 100$$

Results:

The percentages of inhibiting activity on the development of experimental cutaneous erythema were the following: cream containing 0.01% of lysed Hafnia extract 32.2% and cream containing 0.05% of lysed Hafnia extract 44%

(D) Action on the denaturation of proteins (albumin serum) by heat: Mizuschima test Principle of Mizuschima test Anti-inflammatory substances protect the proteins (albumin serum) from denaturation by heat in buffered acid medium.

| Product | Results of turbidity measurement Optical density at 650 mm | | | |
| --- | --- | --- | --- | --- |
| | 1st test | 2nd test | 3rd test | Average OD |
| Control with 0.1% bovine serum albumin | 0.71 | 0.66 | 0.69 | 0.68 |
| Lysed Hafnia extract of Example 1: | | | | |
| 1 mg/ml | 0.41 | 0.40 | 0.48 | 0.43 |
| 2 mg/ml | 0.29 | 0.28 | 0.32 | 0.30 |
| 2.5 mg/ml | 0.23 | 0.20 | 0.22 | 0.22 |
| 3 mg/ml | 0.20 | 0.19 | 0.21 | 0.20 |
| 5 mg/ml | 0.02 | 0.03 | 0.02 | 0.02 |
| 10 mg/ml | 0.01 | 0.01 | 0.01 | 0.01 |

The extract based on lysed Hafnia glycoproteins exerted a protective effect against denaturation of the albumin serum by heat.

Various modifications of the compositions and method of the invention may be made without departing from the spirit or scope thereof and it is to be understood that the invention is intended to be limited only as defined in the appended claims.

What I claim:

1. A cosmetic composition for skin care comprising an effective amount for skin care of glycoprotein extracts of lysed microbial bodies of Hafnia species or strains prepared by (a) cultivating a microbial Hafnia strain until complete development of microbial bodies, (b) subjecting the microbial bodies to lysis, (c) treating the lysate with at least one solvent for delipidation and depigmentation of the lysate, (d) dissolving the resulting product in water, (e) subjecting the solution to centrifugation and (f) optionally subjecting the resulting product to ultrafiltration a cosmetic excipient having skin affinity.

2. The composition of claim 1 containing glycoprotein extracts not having been subjected to ultrafiltration.

3. The composition of claim 1 containing $5 \times 10^{-5}$% to 1% by weight of the glycoprotein extracts.

4. The composition of claim 1 containing at least one member of the group consisting of oleyl acetate, glycol extract of Centella Asiatica, oenothera oil and amino acids.

5. A composition of claim 1 in a form selected from the group consisting of cream, gel, milk, lotion and skin oil.

6. A method of caring for a person's skin comprising applying to a person's skin an effective amount of a cosmetic composition for skin care of glycoprotein extracts of lysed microbial bodies of Hafnia species or strains prepared by (a) cultivating a microbial Hafnia strain until complete development of microbial bodies, (b) subjecting the microbial bodies to lysis, (c) treating the lysate with at least one solvent for delipidation and depigmentation of the lysate, (d) dissolving the resulting product in water, (e) subjecting the solution to centrifugation and (f) optionally subjecting the resulting product ot ultrafiltration sufficient to soothe and improve the appearance of the skin, 7. The method of claim 6 wherein the composition contains the centrifuged product not having been subjected to ultrafiltration.

8. The method of claim 6 wherein the composition contains $5 \times 10^{-5}\%$ to 1% by weight of the glycoprotein extracts.

9. The method of claim 6 wherein the composition contains at least one member selected from the group consisting of oleyl acetate, glycol extract of Centella Asiatica, oenothera oil and amino acids.

10. The method of claim 6 wherein the composition contains a form selected from the group consisting of cream, gel, milk, lotion and skin oil.

* * * * *